(12) United States Patent
Kanayama et al.

(10) Patent No.: US 7,933,014 B2
(45) Date of Patent: Apr. 26, 2011

(54) AUTOMATIC ANALYSIS APPARATUS AND AUTOMATIC ANALYSIS METHOD

(75) Inventors: Shoichi Kanayama, Tochigi-ken (JP); Naoko Omuro, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 197 days.

(21) Appl. No.: 12/168,763

(22) Filed: Jul. 7, 2008

(65) Prior Publication Data
US 2009/0009760 A1 Jan. 8, 2009

(30) Foreign Application Priority Data
Jul. 6, 2007 (JP) ................................. 2007-178387

(51) Int. Cl.
*G01J 3/30* (2006.01)
(52) U.S. Cl. ........ 356/318; 356/440; 356/442; 359/665; 600/309; 600/310
(58) Field of Classification Search .................. 356/318, 356/440–442; 359/665; 600/309, 310
See application file for complete search history.

(56) References Cited

U.S. PATENT DOCUMENTS

| 6,675,030 B2 * | 1/2004 | Ciurczak et al. ............ 600/316 |
| 2003/0127609 A1 * | 7/2003 | El-Hage et al. ............ 250/574 |

* cited by examiner

*Primary Examiner* — Gregory J Toatley
*Assistant Examiner* — Iyabo S Alli
(74) *Attorney, Agent, or Firm* — Oblon, Spivak, McClelland, Maier & Neustadt, L.L.P.

(57) ABSTRACT

An automatic analysis apparatus and an automatic analysis method that can perform both spectrophometric measurements for biochemical tests and the turbidimetric immunoassay with high precision by selectively exchanging a white light or at least one monochromatic light based on analysis conditions determined by a measure condition setting unit for respective measuring object. The automatic analysis apparatus includes an irradiating direction setting unit configured to irradiate the selected white light or at least one monochromatic light based on the analysis conditions onto a reaction cuvette along the same light axis and a light detection unit having a plurality of light receiving elements in order to detect the white light of particular determined wavelength lights and the selected monochromatic light.

15 Claims, 10 Drawing Sheets

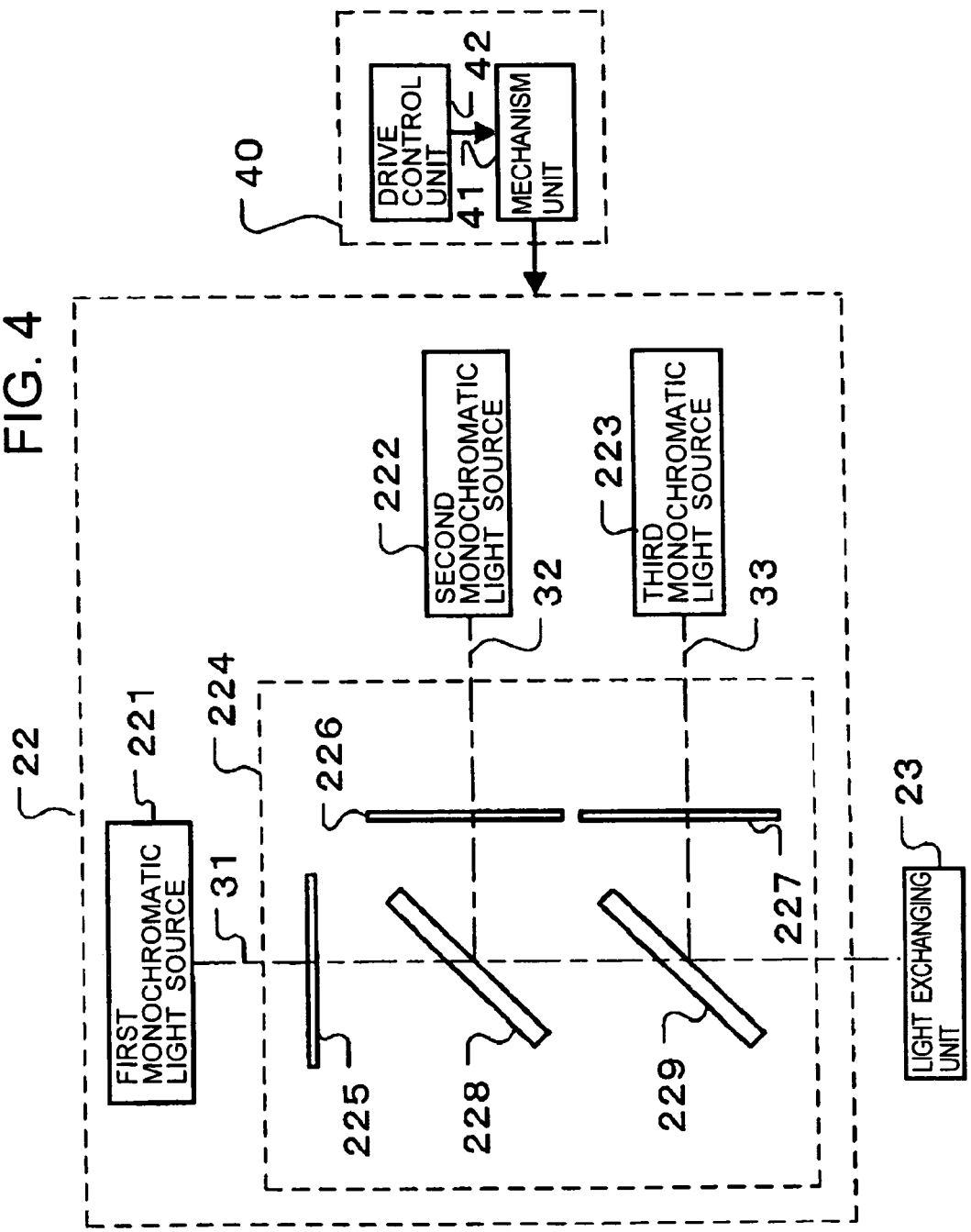

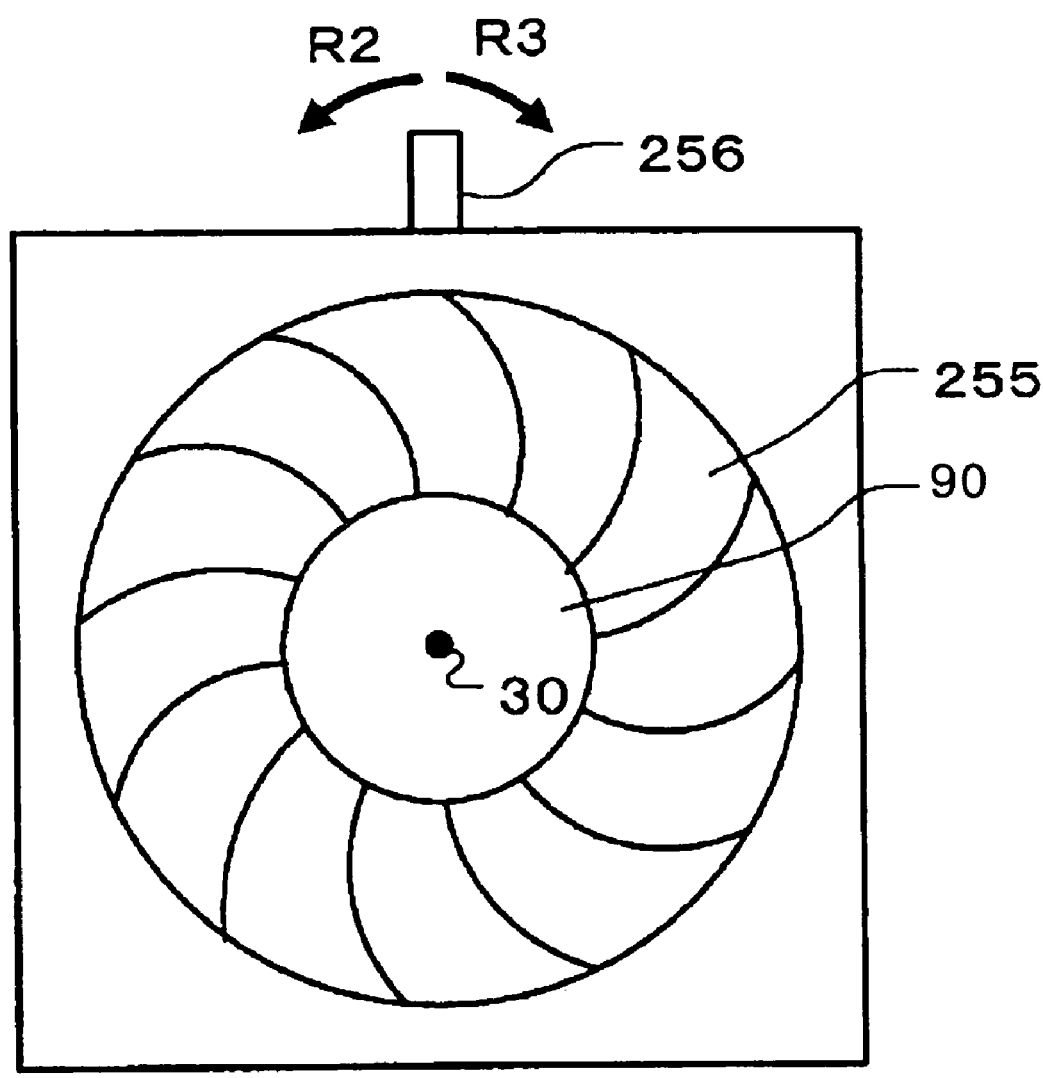

| ITEM | GOT — 631 |
| --- | --- |
| SAMPLE AMOUNT | 5 — 632 |
| REAGENT AMOUNT | FIRST REAGENT: 150 — 633<br>SECOND REAGENT: 50 — 634 |
| KIND OF REACTION | SPECTRO PHOTOMETRY ▶ — 635 |
| WAVELENGTH | WAVE LENGTH 1: 340. ▶ — 636<br>WAVE LENGTH 2: 380 ▶ — 637 |
| MEASURING POINT | 20 ▶ — 638 ~ 29 ▶ — 639 |
| --- | --- |

| ITEM | CRP — 641 |
| --- | --- |
| SAMPLE AMOUNT | 3 — 642 |
| REAGENT AMOUNT | FIRST REAGENT: 100 — 643<br>SECOND REAGENT: 50 — 644 |
| KIND OF REACTION | TURBIDIMETRY ▶ — 645 |
| WAVELENGTH | WAVE LENGTH 1: FIRST MONOCHROMATIC LIGHT ▶ — 646<br>WAVE LENGTH 2: SECOND MONOCHROMATIC LIGHT ▶ — 649 |
| MEASURING POINT | 33 ▶ — 648 ~ 35 ▶ |
| --- | --- |

AUTOMATIC ANALYSIS APPARATUS AND AUTOMATIC ANALYSIS METHOD

CROSS-REFERENCE TO RELATED APPLICATIONS

This application claims priority from, and the benefit of, Japanese Patent Application No. 2007-178387, filed on Jul. 6, 2007, the contents of which are expressly incorporated herein by reference in their entirety.

BACKGROUND OF THE INVENTION

A. Field of the Invention

The present invention relates to an automatic analysis apparatus and an automatic analysis method for analyzing items contained in a mixed solution and more particularly, to an automatic analysis apparatus including a plurality of light sources for automatically analyzing multiple items contained in a mixed solution, such as human fluids with high precision by exchanging the plurality of light sources in accordance with designated analyzing items.

B. Background of the Invention

An automatic analysis apparatus mainly measures biochemical examination items contained in fluids such as blood or urine. Generally, an automatic analysis apparatus for performing biochemical tests employs spectrophotometry in order to analyze a particular item by dispensing a prescribed amount of an object sample and a prescribed amount of reagent corresponding to the item into a reaction cuvette. In the cuvette, the dispensed object sample and the corresponded reagent are mixed and stirred so as to react at a prescribed temperature. Spectrophotometry measures a density or an activity of an object measuring substance or an enzyme contained in the object sample based on a change of color tone due to light absorption of the mixed solution.

In the spectrophotometric biochemical test, a mixed solution of an object sample and a reagent dispensed in a reaction cuvette is irradiated by a light from a light source. A light detector in the spectroscopic analyzer uses a transmission light to detect a change of color tone of the solution due to reaction of the object sample and the reagent. Thus, an item to be measured is detected based on a change of a particular wavelength component absorbed in the reacted solution.

Besides the biochemical test, an immune serum test is also used for analyzing fluids. The immune serum test employs turbidimetric immunoassay in order to acquire an item density of an object sample by measuring a turbidity change of the object sample due to an agglutination of the mixed solution that is generated by scattering lights which is due to a reaction between an antigen and an antibody in the solution of the object sample.

Besides the turbidimetric immunoassay, a latex agglutination turbidimetric immunoassay is also employed to measure a turbidity change of the object sample due to agglutination that is caused by a reaction between an antigen in an object sample and an antibody sensitized latex that is sensitized latex particles. In either of the turbidimetric immunoassay, a reagent is adjusted for the applicable measurements to be performed in each particular immune serum test apparatus. Consequently, possible items to be measured also are limited by each particular immune serum test apparatus.

Recently, an increase in efficiency and a reduction of a cost of the biochemical test and the immune serum test are keenly required. To meet this demand, a single analyzing apparatus that can be used to perform a plurality of measurements for a plurality of test items including both the biochemical test and the immune serum test in a single analyzing apparatus is required. Particularly, since automatic analysis apparatus for biochemical tests can be used to perform high speed processing for many tests of a plurality items to be measured, it is possible to use an automatic analysis apparatus for immune serum testing.

As explained above, spectrophotometry is typically employed for an automatic analysis apparatus in which an optical system measures a change of color tone of a solution in a cuvette by detecting a light transmitted through the cuvette. The change of color tone of the solution is generated by the light absorption of the solution due to reaction between an object sample and a reagent. Thus, the conventional automatic analysis apparatus does not take any measurement of a light source for performing an immune serum test in which a measurement of the particular amount of transmitted light is necessary to perform a turbidimetric immunoassay in order to measure a change of turbidity of a sample solution due to the scattered transmission light caused by agglutination of the solution. Consequently, even if an optical system itself in the conventional analysis apparatus of biochemical tests is used for measuring a turbidity change of a transmitted light to perform an immune serum test, the transmitted light is reduced lower than a necessary amount because of the scattering of light due to agglutination of a solution. Such lowered amount of light generates a lower accuracy of a measurement.

Japanese patent application publication 2001-141654 proposed a spectrum luminous intensity/turbidity detection unit that is combined both of a penetration light measuring optical unit and a scattered lights measuring optical unit for applying to an automatic analysis apparatus. However, the proposed spectrum luminous intensity/turbidity detection unit needs to separately provide both a transmitted light detection unit for measuring a change of color tone and a transmitted light detection unit for measuring a change of turbidity. Thus, the proposed automatic analysis apparatus simply combines both a transmitted light detection unit for spectrophotometry and a transmitted light detection unit for a turbidimetric immunoassay. Consequently, the proposed apparatus including both spectrophotometry and turbidimetric immunoassay functions has serious problems for constructing a complicated optical system including light sources and transmitted light detection units. Further, the proposed apparatus is inevitable larger.

SUMMARY OF THE INVENTION

To solve the above-mentioned conventional problems and defects, the present invention provides a new automatic analysis apparatus and an automatic analysis method that can automatically analyze a plurality of items to be measured using both biochemical tests and immune serum tests with high precision without enlarging the analysis apparatus.

In the automatic analysis apparatus and automatic analysis method consistent with the present invention, a light source unit includes a plurality of light source comprised of a white light source and at least one laser light source (hereinafter, "monochromatic light source"). In accordance with the item to be measured, an appropriate light source in the light source unit of the automatic analysis apparatus and automatic analysis method according to the present invention is automatically exchanged so as to perform a biochemical spectrophotometric test or a turbidimetric immune serum test. In the automatic analysis apparatus and automatic analysis method consistent with the present invention, both a transmitted light detection for measurement by spectrophotometry and a transmitted light detection for measurement by turbidimetric immunoassay are performed in the same detection unit by simply exchanging an appropriate light source.

Thus, the present invention includes a white light source and at least one monochromatic light source in order to selectively exchange or simultaneously irradiate a white light and at least one monochromatic light on the same light axis in accordance with the item to be measured in a mixed solution in order to perform both the spectrophotometric and the turbidimetric immunoassay measurements. The present invention provides a new and novel automatic analysis apparatus and automatic analysis method that can detect with high precision both changes of color tones and turbidity of transmitted light by a single detection unit.

According to the present invention, a light measuring optical system of an automatic analysis apparatus that is comprised of a light irradiating unit, a light detection unit, a spectroscopic analysis unit and a detector can be commonly used for both the measurements of a spectrophotometric test by using a white light and a turbidimetric immunoassay test by using at least one monochromatic light. Consequently, it becomes possible to simplify the construction of a light measuring optical system for use as a highly precise automatic analysis apparatus and thus reduce the cost for detecting a plurality of different reaction types of the mixed solution.

Further, according to the automatic analysis apparatus and automatic analysis method consistent with the present invention, it becomes possible to reduce amounts of the object sample and the reagent used by efficiently dispensing each appropriate amount of the object sample and the reagent corresponding to the item to be measured.

An automatic analysis apparatus consistent with the present invention includes a light measuring unit configured to measure items in a mixed solution of an object sample and at least one reagent contained in a reaction cuvette by irradiating a light and detecting the light transmitted through the reaction cuvette. The light measuring unit in the automatic analysis apparatus is comprised of:

a light source unit including a white light source unit configured to irradiate a white light and a monochromatic light source unit configured to irradiate at least one monochromatic light;

a lighting direction setting unit configured to irradiate a light on the reaction cuvette positioned at a measuring point in the light measuring unit by selectively exchanging the white light at least one monochromatic light on a measuring light axis in the light measuring unit in accordance with an item to be measured;

a spectroscopic analysis unit configured to perform a spectroscopic analysis of a prescribed wavelength light in the white light or the at least one monochromatic light that are transmitted through the reaction cuvette; and a light detection unit configured to detect the prescribed wavelength in the white light or at least one monochromatic light in the spectroscopic analysis.

An automatic analysis method consistent with the present invention measures a mixed solution of an object sample and at least one reagent contained in a reaction cuvette by irradiating a white light or at least one monochromatic light, each irradiated from a white light source or at least one monochromatic light source in order to detect a change of color tone or turbidity of a transmitted light passed through the mixed solution, the automatic analysis method is comprised of:

irradiating the white light or at least one monochromatic light onto the reaction cuvette positioned at predetermined light measuring positions by selectively exchanging the white light or at least one monochromatic light along a same measuring light axis; and detecting the white light of particularly determined wavelengths or at least one monochromatic light transmitted through the reaction cuvette along the measuring light axis.

BRIEF DESCRIPTION OF THE DRAWINGS

The accompanying drawings, which are incorporated in and constitute part of this specification, illustrate various embodiments and/or features of the present invention, and together with the description, serve to explain embodiments of the present invention. Where possible, the same reference number will be used throughout the drawings to describe the same or similar parts. In the drawings:

FIG. 4 illustrates an embodiment of a chromatic light source unit in the light measuring unit shown in FIG. 3.

FIG. 5 illustrates an embodiment of a lighting aperture diaphragm and a detection aperture diaphragm in the light measuring unit shown in FIG. 3.

FIGS. 6A and 6B illustrate example analysis conditions setting screens that display analysis conditions inputted through an operation unit in the automatic analysis apparatus shown in FIG. 1.

DESCRIPTION OF THE EMBODIMENTS

Figure 1:
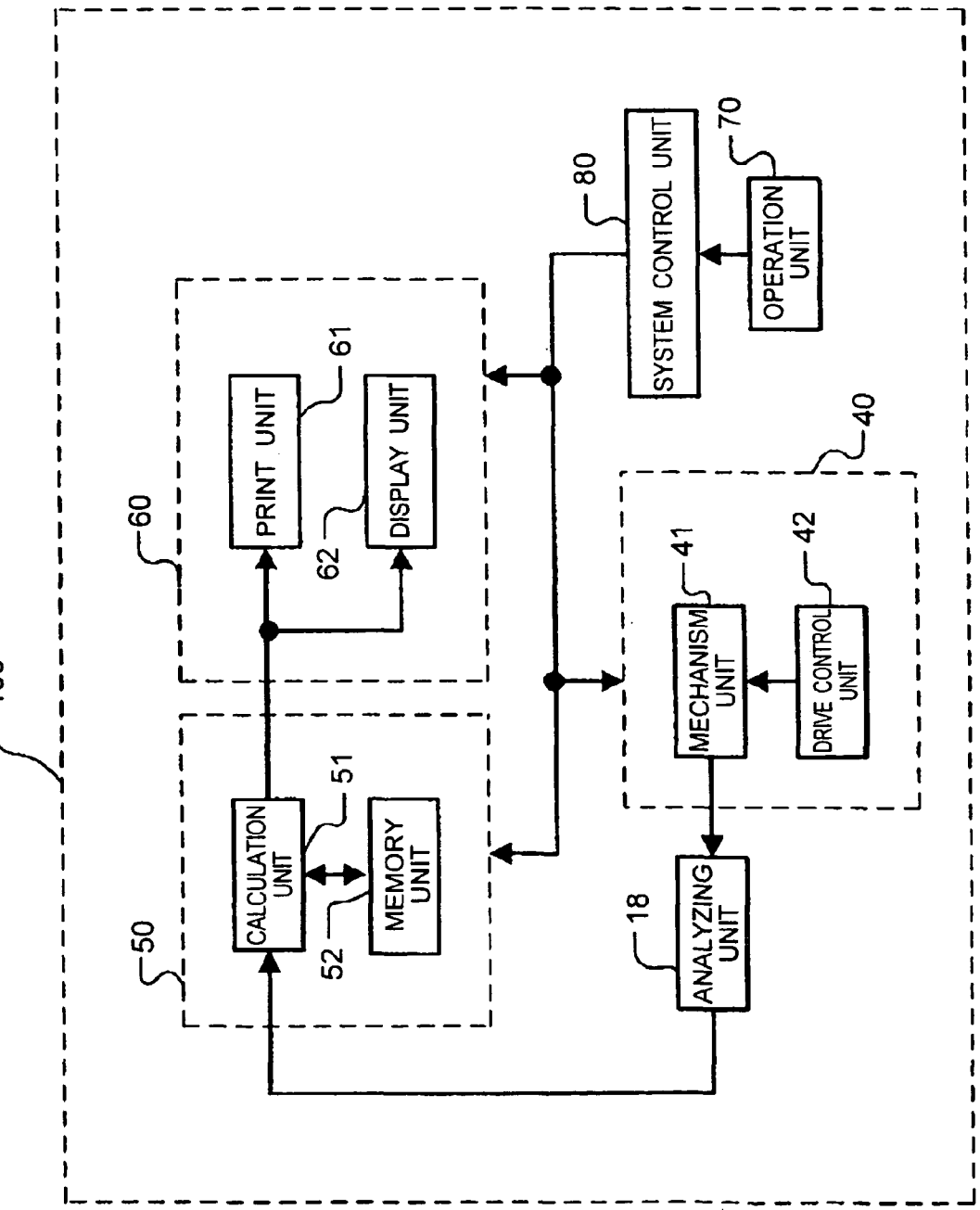
FIG. 1 is a block diagram illustrating an embodiment of an automatic analysis apparatus consistent with the present invention.

As shown in FIG. 1, an embodiment of an automatic analysis apparatus 100 consistent with the present invention includes an analyzing unit 18, an analysis control unit 40, a data processing unit 50, an output unit 60, an operation unit 70 and a system control unit 80. The analyzing unit 18, as explained later, includes a plurality of measuring units in order to measure each of the items to be measured for a plurality of reference samples and object samples. The analysis control unit 40 includes a mechanism unit 41 for driving each of measuring units in the analyzing unit 18 and a drive control unit 42 for controlling each drive of the mechanism unit. The data processing unit 50 includes a calculation unit 51 for generating a calibration curve and analysis data based on reference sample data and object sample data supplied from the analyzing unit 18 and a memory unit 52 for storing the calibration curve and the analysis data generated by the calculation unit 51.

The automatic analysis apparatus 100 further includes an output unit 60, an operation unit 70 and a system control unit 80. The output unit 60 includes a print unit 61 and a display unit 62 for inputting the calibration curve and the analysis data generated in the data processing unit 50. The operation unit 70 performs input operations of analysis conditions for a reference sample and a calibration curve for each of the items to be measured and also inputs various kinds of command signals. The system control unit 80 totally controls operations of the analysis control unit 40, the data processing unit 50 and the output unit 60.

Figure 2:
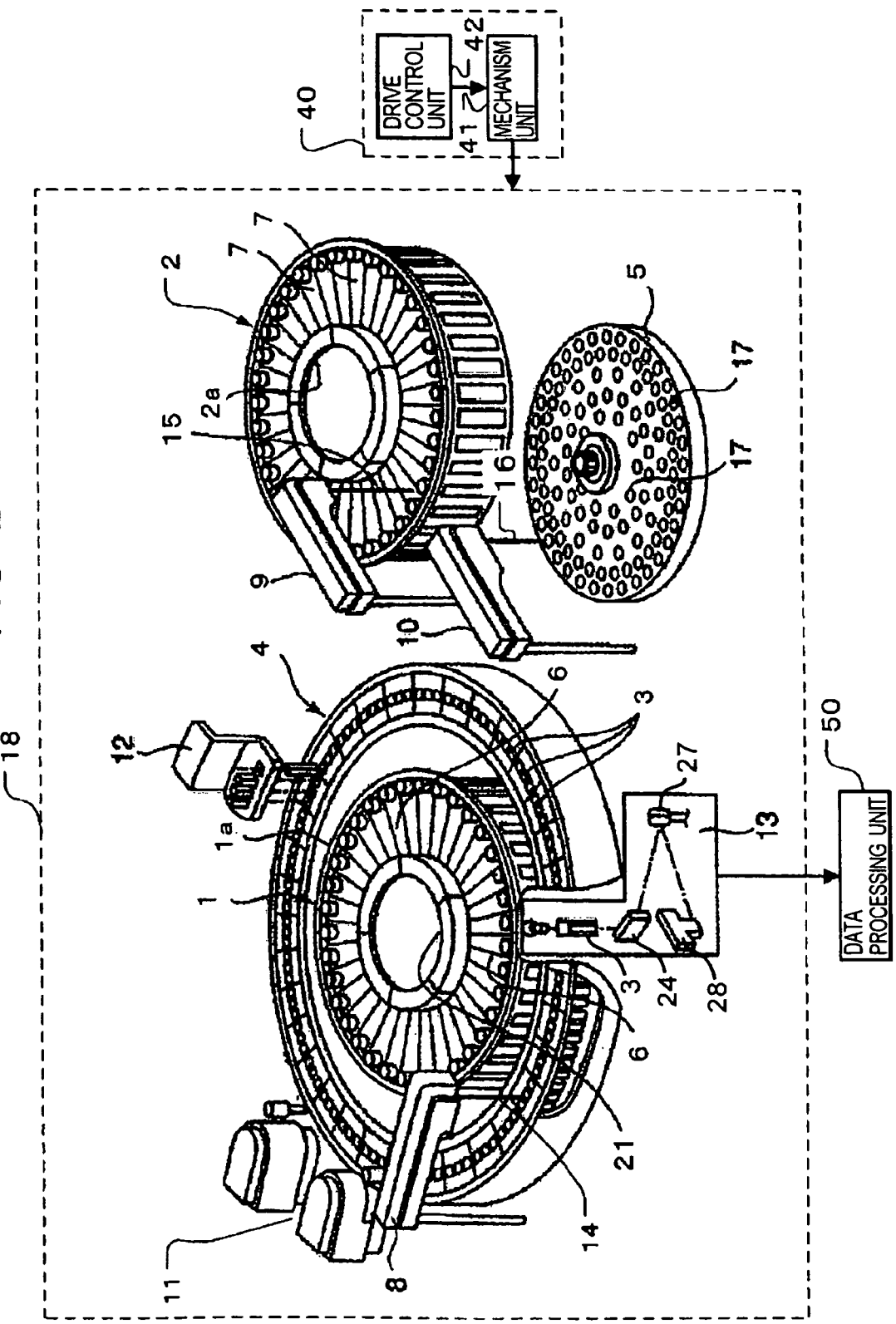
FIG. 2 illustrates an embodiment of the analysis unit in the automatic analysis apparatus shown in FIG. 1.

FIG. 2 shows the main components of the analyzing unit 18. The analyzing unit 18 includes a first reagent warehouse 1, a second reagent warehouse 2 and a disk sampler 5. The disk sampler 5 rotatably holds a plurality of sample container 17 for containing samples, such as a reference sample and an object sample. The first reagent warehouse 1 includes a holding unit 1a that rotatably holds a plurality of reagent container 6 containing the first reagent for reacting the items contained in the sample container 17 corresponding to the respective items. The second reagent warehouse 2 includes a holding member 2a for rotatably holding reagent containers 7 containing a second reagent that is used with the first reagent as a pair. Typically, when the second reagent is chosen, the first reagent is chosen as its pair.

The analyzing unit 18 further includes a first reagent dispensing probe 14, a second reagent dispensing probe 15 and a plurality of dispensing probes 14, 15 and 16, each of those probes is rotatably held so as to be moved upward and downward. Thus, the sample dispensing probe 16 is rotatably held by a sample dispensing arm 10 so as to move upward and downward. Similarly, the first reagent dispensing probe 14 and the second reagent dispensing probe 15 are held by the first and second reagent dispensing arms 8 and 9, respectively, so as to be rotated and moved upward and downward. The sample dispensing probe 16 suctions a sample from a sample container 17 held in the disk sampler 5 and discharges the suctioned sample into a reaction cuvette 3. The first dispensing probe 14 suctions a first reagent from the reagent container 6 in the first reagent warehouse 1 and discharges the suctioned first reagent into a reaction cuvette 3. The second reagent dispensing probe 15 suctions a second reagent from a reagent container 7 in the second reagent warehouse 2 and discharges the suctioned second reagent into the reaction cuvette 3 that contains the first reagent.

The analyzing unit 18 further includes a reaction disk 4, a stirring unit 11, a light measuring unit 13 and a washing unit 12. The reaction disk 4 is positioned at an outer surface side of the first reagent warehouse 1 in order to rotatably hold the plurality of reaction cuvettes 3 so as to move a particular reaction cuvette to a lighting position. The stirring unit 11 stirs a mixed solution of a sample and a first reagent or a mixed solution of a sample and both a first reagent and a second reagent that are dispensed into a reaction cuvette 3. The light measuring unit 13 measures the reaction cuvette 3 containing each of the mixed solutions. The washing unit 12 includes a washing nozzle for suctioning each mixed solution that remains in a reaction cuvette 3 after a measurement and for washing the inside of the reaction cuvette 3. The drying nozzle is held so as to move upward and downward. Thus, after a measurement, the reaction cuvette 3, the sample dispensing probe 16, the first and second reagent dispensing probes 14 and 15 and the stirring unit 11 are used for a next measurement after washing.

The light measuring unit 13 irradiates a light to a rotatably moving reaction cuvette 3 at a light measuring position P in order to generate reference sample data by converting a light transmitted in the mixed solution, including a light reference sample, into a light absorption degree. The absorption degree is outputted to the data processing unit 50. The light measuring unit 13 further generates object sample data by converting a transmitted light in the mixed solution including an object sample into a light absorption degree and outputs object sample data to the data processing unit 50.

As explained before, the analysis control unit 40 includes a mechanism unit 41 having a drive mechanism for driving each of measuring portions of the analyzing unit 18 and a control unit 42 for controlling each portion of the mechanism unit 41 by driving each of the mechanisms. The mechanism unit 41 includes a rotating mechanism for rotating a first holding member 1a of the first reagent warehouse 1, a second holding member 2a of the second reagent warehouse 2 and the disk sampler 5, a mechanism for rotating the reaction disk 4 and for rotating and driving upward and downward a sample dispensing arm 10, a first reagent dispensing arm 8, a second reagent dispensing arm 9 and a stirring unit 11, and also for moving upward and downward the washing unit 12.

The mechanism unit 41 further includes a sample dispensing pump driving mechanism for suctioning and discharging a sample solution through the sample dispensing probe 16, a first and second reagent pump driving mechanism for suctioning and discharging the first and second reagent from the first and second reagent dispensing probes 14 and 15, a stirring drive mechanism and a stirring member in the stirring unit, a drive mechanism for driving each portion of the light measuring unit 13, a washing pump drive mechanism for suctioning a mixed solution and for discharging and suctioning a washing liquid from a washing nozzle of the washing unit 12 and a drying pump driving mechanism washing unit 12 for suctioning from a drying nozzle.

As explained in FIG. 1, the data processing unit 50 includes a calculation unit 51 and a memory unit 52. The calculation unit 51 generates a calibration curve based on reference sample data of each item to be measured supplied from each light measuring unit 13 in the analyzing unit 18. The generated data is stored in the memory unit 52 and also outputted to the output unit 60. The memory unit 52 is comprised of, for instance, a hard disk and stores each calibration curve outputted from the calculation unit 51 for each of the items to be measured. The calculation unit 51 further generates density or activity analyzing data by using a calibration curve corresponding to an item to be measured of an object sample data read out from the memory unit 52. The analyzing data generated from the calculation unit 51 area is stored in a hard disk of the memory unit 52 in each of the object samples and is also outputted to the output unit 60.

Such a calibration curve or analysis data supplied from the data processing unit 50 is printed by the print unit 61 in the output unit 60. The print unit 61 provides a printer in order to print the calibration curve or analysis data on printing paper in a prescribed format. The output unit 60 further includes a display unit 62. The display unit 62 includes a monitor, such as a cathode ray tube (CRT) or a liquid crystal panel (LCP), in order to display a calibration curve and analysis data outputted from the data processing unit 50. Further, the monitor displays an analysis condition setting screen for setting analysis conditions of each item to be measured, such as a sample amount, a reagent amount and a wavelength of a light. The monitor also displays an object setting screen for setting, for example, an object's ID and name and an item to be measured selection screen for selecting items to be measured for each of the object samples.

The operation unit 70 includes input devices, such as a keyboard, a mouse, buttons and a touch key panel for inputting, for example, analysis conditions for each of the items to be measured, an object data such as an object's ID and name, and items to be measured for each of the object samples.

The system control unit includes a central processing unit (CPU) and a memory circuit. The CPU in the system control unit 80 totally controls the entire operation of the automatic analysis apparatus. The memory circuit in the system control unit 80 stores data, such as command signals inputted through the operation unit 70, various analysis conditions for each of the items to be measured, object data, and items to be measured for each of object samples. Using this stored data, the CPU in the system control unit 80 controls each of measuring units in the analyzing unit 18 at predetermined analyzing cycle conditions.

Figure 3:
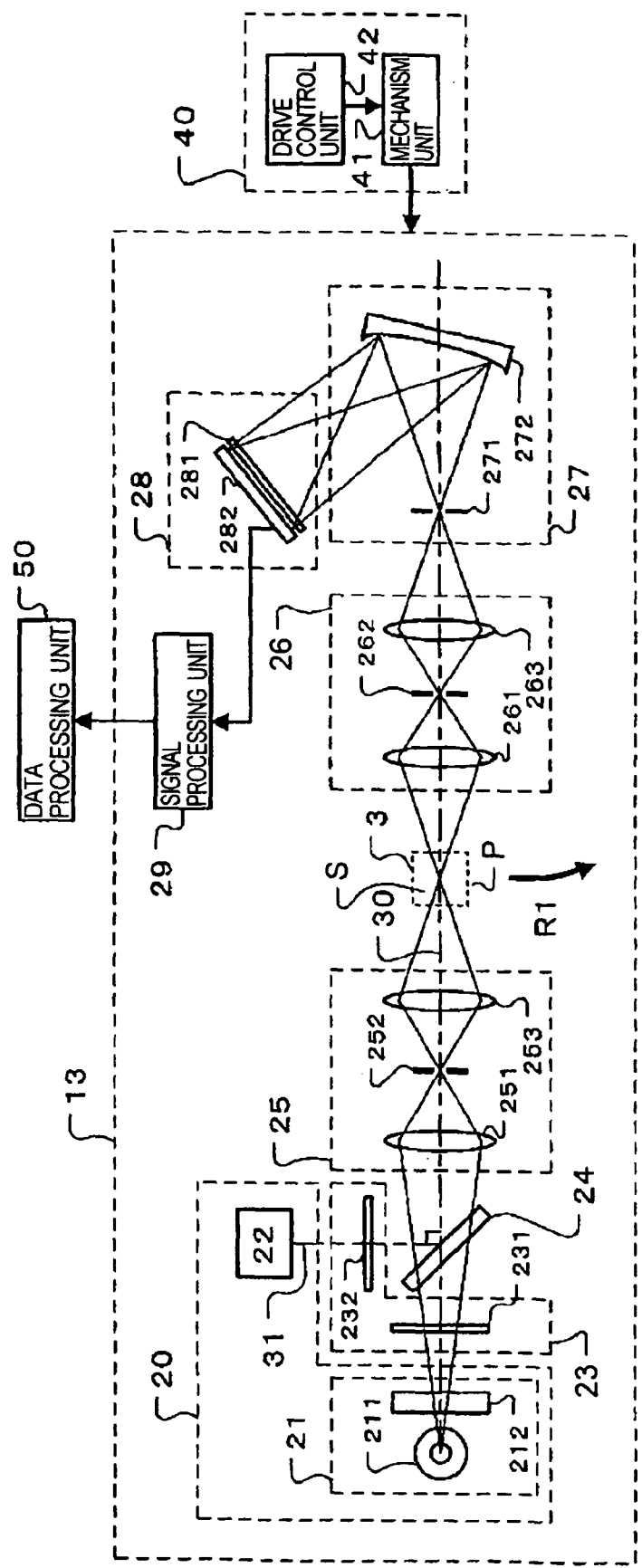
FIG. 3 illustrates an embodiment of the analysis unit shown in FIG. 2.

FIG. 3 shows a construction of the light measuring unit 13 in the analyzing unit 18. The light measuring unit 13 includes a light source unit 20, a light exchanging unit 23, a lighting direction setting unit 24, a lighting optical unit 25, a detecting optical unit 26, a spectroscopic analysis unit 27, a light detection unit 28 and a signal processing unit 29. The light source unit 20 includes a white light source unit 21 and a monochromatic light source unit 22. The light source unit 20 includes a white light source 21 for irradiating a white light and a monochromatic light source portion 22 for irradiating at least one monochromatic light. The white light source unit 21 is comprised of the white light source 211, which could be for instance, a halogen lamp that irradiates a white light including a wide range of wavelengths from near ultraviolet to near infrared and a filter 212 for cutting off unnecessary light waves from the white light source 211, such as heat waves. The white light source 211 is provided so that an emission center of the white light is located on a first light axis 30, and irradiates a white light to the exchanging unit 23 through the filter 212.

The light exchanging unit 23 exchanges the irradiation light irradiated from the light source unit 20 to either the white light or the monochromatic light. The exchanged white light or the monochromatic light in the light exchanging unit 23 is irradiated onto the reaction cuvette 3 that arrived at a light measuring position P through the lighting direction setting unit 24 and the lighting optical unit 25. The lighting optical unit 25 sets an irradiation scope onto the reaction cuvette 3 by the white light or the monochromatic light irradiated from the lighting direction setting unit 24.

The detection optical unit 26 sets an irradiation scope of the white light or the monochromatic light that are irradiated through the lighting optical unit 25 and are passed through a mixed solution S contained in the reaction cuvette 3. The spectroscopic analysis unit 27 separates the white light or the monochromatic light passed through the detection optical unit 26 into wavelength. Each of the separated wavelength lights by the spectroscopic analysis unit 27 is respectively detected at the detection unit 28 and the detected signals are processed in the signal processing unit 29.

FIG. 4 illustrates an example construction of the monochromatic light source unit 22 in the light source unit 20. The monochromatic light source unit 22 is comprised of a first, second and third monochromatic light sources, namely, 221, 222 and 223, each irradiates a monochromatic light with a single wavelength difference between each other, and a multiplexing optical unit 224 for multiplexing a plurality of monochromatic lights among the first to the third monochromatic lights irradiated from the monochromatic light sources 221, 222 and 223.

Each of the first to third monochromatic light sources 221, 222 and 223 includes a light irradiating element, such as a monochromatic semiconductor or a light emitting diode (LED) in order to irradiate a monochromatic light of a single wavelength included as a component of the wavelengths of white light but having a much higher brightness and linearity than the white light. The monochromatic light source 221 of the first wavelength, as shown in FIG. 3, is provided on the second light axis 31 that orthogonally crosses the first light axis 30 passing through the reaction cuvette 3. Thus, the monochromatic light source 221 of the first wavelength irradiates a monochromatic light of the first wavelength along a second light axis 31 in an orthogonal direction to the first light axis 30.

The monochromatic light source 222 of a second wavelength, as shown in FIG. 4, is provided on the third light axis 32 that orthogonally crosses the second light axis 31 and irradiates a monochromatic light of a second wavelength that is different from first wavelength along the third light axis 32 toward the second light axis 31. Further, the monochromatic light source 223 of a third wavelength is provided on the fourth light axis 33 that orthogonally crosses the second light axis 31 so as to split from the third light axis 32 in order to irradiate a monochromatic light of a third wavelength that is different from each of the first and second wavelengths along the fourth light axis 33 toward the second light axis 31.

As an exemplary feature, the lights' multiplexing unit 224 in the monochromatic light source portion 22 includes the first, second and third monochromatic light shutters 225, 226 and 227 for opening and cutting off each of the first to third monochromatic lights irradiated from the first, second and third wavelength monochromatic light sources 221, 222 and 223, a first multiplexing unit 228 for irradiating a multiplexed monochromatic light that is multiplexed by two monochromatic lights passed through the first and second monochromatic light shutters 225 and 226 to the light exchanging unit 23 and a second multiplexing unit 229 for irradiating a multiplexed monochromatic light that is multiplexed by two monochromatic lights passed through the first and third monochromatic light shutters 225 and 227 to the light exchanging unit 23.

The respective open and close operations of the first to third monochromatic light shutters 225, 226 and 227 are performed by the mechanism unit 41 in the analysis control unit 40 so that one or two monochromatic light shutters are simultaneously opened and the remaining monochromatic light shutter is closed.

Thus, the first monochromatic light shutter 225 that is provided between the monochromatic light source 221 of the first wavelength and the first multiplexing unit 228 opens and closes the monochromatic light of the first wavelength irradiated from the monochromatic light source 221 of the first wavelength against the first multiplexing unit 228. The second monochromatic light shutter 226 that is provided between the monochromatic light source 222 of the second wavelength and the first multiplexing unit 228 opens and closes the monochromatic light of the second wavelength irradiated from the monochromatic light source 222 of the second wavelength against the first multiplexing unit 228. The third monochromatic light shutter 227 that is provided between the monochromatic light source 223 of the third wavelength and the second multiplexing unit 229 opens and closes the monochromatic light of the third wavelength irradiated from the monochromatic light source 223 of the third wavelength against the second multiplexing unit 229.

The first multiplexing unit 228 is comprised of a dichroic mirror in order to reflect a particular wavelength light and to transmit lights of a wavelength band other than the particular wavelength. The first multiplexing unit 228 is provided between the monochromatic light shutter 225 of the first wavelength and the second multiplexing unit 229 transmits the first wavelength monochromatic light irradiated from the first wavelength monochromatic light source 221 when the second monochromatic light shutter 226 is closed and the first monochromatic light shutter 225 is opened. When the first monochromatic light shutter 225 is closed and the second monochromatic light shutter 226 is opened, the first multiplexing unit 228 reflects the second monochromatic light irradiated from the second monochromatic light source 222 along the second light axis 31 to a direction of the first light axis 30 (FIG. 3). Further, when both the first and second monochromatic light shutters 225 and 226 are opened, the first multiplexing unit 228 transmits the first monochromatic light irradiated from the first monochromatic light source 221 and also multiplexes the first monochromatic light with the second monochromatic light irradiated from the second monochromatic light source 222 by reflecting the second monochromatic light along the second light axis 31 in the first light axis 30 direction so as to overlap on the second light axis 31.

It is, of course, possible to replace the dichroic mirror in the first multiplexing unit 228 with a half mirror. In the case when a half mirror is used, when the second monochromatic light shutter 226 is closed and the first monochromatic light shutter 225 is opened, a prescribed ratio of the first monochromatic light from the first monochromatic light source 221 are transmitted and the remaining light is reflected in a direction opposite to the second monochromatic light shutter 226. On the other hand, when the first monochromatic light shutter 225 is closed and the second monochromatic light shutter 226 is opened, a prescribed ratio of the second monochromatic light from the second monochromatic light source 222 is transmitted and the remaining light is reflected in the direction of the second multiplexing unit 229 along the second light axis 31. It is also possible to multiplex by transmitting the first monochromatic light from the first monochromatic light source 221 when the first and second monochromatic light shutters 225 and 226 are opened reflecting the second monochromatic light from the second monochromatic light source 222 in the direction of the second multiplexing unit 229 along the second light axis 31.

The second multiplexing unit 229 is comprised of a dichroic mirror and is positioned between the first multiplexing unit 228 and the light exchanging unit 23. The second multiplexing unit 229 transmits the first or second monochromatic light through the first multiplexing unit 228 to the light exchanging unit 23 when the third monochromatic light shutter 227 is closed and the first monochromatic light shutter 225 or the second monochromatic light shutter 226 is opened. Further, when the first or second monochromatic light shutter 225 or 226 is opened and the third monochromatic light shutter 227 is opened, the second multiplexing unit 229 reflects the third monochromatic light from the third monochromatic light source 223 in the direction of the light exchanging unit 23 along the second light axis 31.

Also, when either one of the first or second monochromatic light shutter 225 or 226 is closed and the other is opened, the second multiplexing unit 229 transmits the monochromatic light monochromatic light corresponded to the other shutter through the first multiplexing unit 228 and reflects the third monochromatic light from the third monochromatic light source 223 in the direction of the light exchanging unit 23 the light exchanging unit 23 along the second light axis 31. Also, the second multiplexing unit 229 irradiates light to the light exchanging unit 23 by multiplexing monochromatic light corresponding to the other shutter and the third monochromatic light.

It is also possible to change the dichroic mirror for the second multiplexing unit 229 to a half mirror. In this case, when the third monochromatic light shutter 227 is opened and the first or second monochromatic light shutter 225 or 226 is closed, the second multiplexing unit 229 transmits a prescribed amount ratio of the first or second monochromatic light through the first multiplexing unit 228 and reflects the remaining light in the direction opposite to the third monochromatic light shutter 227. Further, when the first or second monochromatic light shutter 225 or 226 is closed and the third monochromatic light shutter 227 is opened, the second multiplexing unit 229 transmits a prescribed amount ratio of the third monochromatic light from the third monochromatic light source 223 and reflects the remaining light in the direction of the light exchanging unit 23 along the second light axis 31. Further, when either one of the first or second monochromatic light shutter 225 or 226 is closed and both of the other shutters and the third monochromatic light shutter 227 are opened, the second multiplexing unit 229 transmits the monochromatic light corresponding to the other shutter through the first multiplexing unit 228 and multiplexes the third monochromatic light from the third monochromatic light source 223 by reflecting the light in the direction of the light exchanging unit 23 along the second light axis 31.

As shown in FIG. 3, the light exchanging unit 23 exchanges the light irradiated from the light source unit 20 to either the white light from the white light source unit 21 or the monochromatic light from the monochromatic light source unit 22. The light exchanging unit 23 includes a white light shutter 231 corresponding to the white light and a monochromatic light shutter 232 corresponding to the monochromatic light. The white light shutter 231 is provided between the white light source unit 21 and the lighting direction setting unit 24 in order to open and close the white light from the white light source unit 21 to the lighting direction setting unit 24. The monochromatic light shutter 232 is provided between the monochromatic light source unit 22 and the lighting direction setting unit 24 in order to open and close the monochromatic light from the monochromatic light source unit 22 to the lighting direction setting unit 24. The white light shutter 231 and the monochromatic light shutter 232 are driven by the mechanism unit 41 in the analysis control unit 40 so that either one of the white light shutter 231 or the monochromatic light shutter 232 is opened and the other is closed.

The lighting direction setting unit 24 is comprised of a dichroic mirror that is positioned between the white light shutter 231 of the light exchanging unit 23 and the lighting optical unit 25. When the monochromatic light shutter 232 is closed and white light shutter 231 is opened in the light exchanging unit 23, the lighting direction setting unit 24 reflects the first to third wavelength lights each corresponding to the first to third monochromatic lights from the monochromatic light source unit 22 that are included in the white light in a direction opposite to the monochromatic light shutter 232 and transmits the white light except, the lights corresponding to the first to third wavelength monochromatic lights, to the lighting optical unit 25. When the white light shutter 231 is closed and the monochromatic light shutter 232 is opened, the lighting direction setting unit 24 reflects the monochromatic light from the monochromatic light monochromatic light source unit 22 in the direction of the lighting optical unit 25 along the first light axis 30.

It is also possible to construct the lighting direction setting unit 24 by using a half mirror. When the monochromatic light shutter 232 is closed and the white light shutter 231 is opened, the half mirror transmits a prescribed amount ratio of the white light from the white light source unit 21 and reflects in a direction opposite to the monochromatic light shutter 232. When the white light shutter 231 is closed and the monochromatic light shutter 232 is opened, the half mirror transmits a prescribed amount ratio of the monochromatic light from the monochromatic light source unit 22 and reflects in the direction of the lighting optical unit 25 along the first light axis 30.

It is further possible to construct the lighting direction setting unit 24 by using a light polarizing filter. When the monochromatic light shutter 232 is closed and the white light shutter 231 is opened, the light polarizing filter transmits only the light waves in the white light irradiated from the white light source unit 21 that are vibrating in a prescribed direction. When the white light shutter 231 is closed and the monochromatic light shutter 232 is opened, the light polarizing filter reflects the light waves of the monochromatic light from the monochromatic light source unit 22 that are vibrating in directions other than the prescribed direction in the direction of the lighting optical unit 25 along the first light axis 30.

It is further possible to construct the lighting direction setting unit 24 by using a liquid crystal panel that can control the transmitted amount of light. Similar to the light polarizing filter, when the monochromatic light shutter 232 is closed and the white light shutter 231 is opened, the liquid crystal panel transmits light waves vibrating in a prescribed direction in the white light from the white light source unit 21. When the white light shutter 231 is closed and the monochromatic light shutter 232 is opened, the liquid crystal panel reflects light waves vibrating in the directions other than the prescribed direction in the monochromatic light from the monochromatic light source unit 22 in the direction of the lighting optical unit 25 along the first light axis 30.

To simplify the construction of the light measuring unit 13, it is also possible to avoid the exchanging unit 23 by constructing the lighting direction setting unit 24 by using either the light polarizing filter or the half mirror in order to irradiate the multiplexed lights to the lighting optical unit 25 by multiplexing the white light that is irradiated from the white light source unit 21 and transmitted through the lighting direction setting unit 24 with the monochromatic light that is irradiated from the monochromatic light source unit 22 and reflected through either the light polarizing filter or the half mirror.

The lighting optical unit 25 is comprised of a first light condensing lens 251 for condensing the white light or the monochromatic light from the lighting direction setting unit 24 near the lighting aperture diaphragm 252, a lighting aperture diaphragm 252 for setting an irradiation area of the condensed light onto the reaction cuvette 3 and a second light condensing lens 253 for irradiating the white light or the monochromatic light passed through the lighting aperture diaphragm 252 onto the reaction cuvette 3. A light axis center of the first light condensing lens 251 is positioned on the first light axis 30. The lighting aperture diaphragm 252 is provided between the first light condensing lens 251 and the second light condensing lens 253 so as to be split.

FIG. 5 illustrates a construction of the lighting aperture diaphragm 252 in the lighting optical unit 25. The detection aperture diaphragm 262 in the lighting optical unit 25 also has a similar structure. The lighting aperture diaphragm 252 is comprised of a circular aperture 90 of which the center is positioned on the first light axis 30, a plurality of diaphragm shuttlecocks 255 for varying an aperture size of the circular aperture for keeping the center on the first light axis 30 and a lever 256 for operating the plurality of diaphragm shuttlecocks 255. When the lever 256 is driven in the R2 direction as depicted in FIG. 5 by the mechanism unit 41 in the analysis control unit 40, the circular aperture size of the diaphragm shuttlecocks 255 is enlarged. On the other hand, when the lever 256 is driven in the R3 direction as depicted in FIG. 3, the second light condensing lens 253 in the lighting optical unit 25 is provided so as to place its light axis center on the first light axis 30 in order to condense the white light or the monochromatic light passed through the lighting aperture diaphragm 252 onto a reaction cuvette 3 placed at a light measuring position P. The white light or the monochromatic light that penetrates through the reaction cuvette 3 is supplied to the detection optical unit 26.

The detection optical unit 26 is comprised of a first detection light condensing lens 261 for condensing the white light or the monochromatic light passed through the reaction cuvette 33, a detection aperture diaphragm 262 for setting a passing area of the condensed white light or monochromatic light by the first detection light condensing lens 261 and a second detection light condensing lens 263 for condensing the white light or the monochromatic light passed through the detection aperture diaphragm 262. The first detection light condensing lens 261 and the second detection light condensing lens 263 are provided so that each of its light axis center is positioned on the first light axis 30 in order to condense the condensed white light or monochromatic light on the detection aperture diaphragm 262 that is provided between the first detection light condensing lens 261 and the second detection light condensing lens 263. As the lighting aperture diaphragm 252, the detection aperture diaphragm 262 has a circular aperture construction so as to enlarge or reduce the aperture size. The white light or the monochromatic light supplied from the detection optical unit 26 is condensed to the spectroscopic analysis unit 27.

The spectroscopic analysis unit 27 includes a slit 271 and a diffraction grating 272. The slit 271 stops the white light or allows the monochromatic light to be passed through the detection lens 263 in the detection optical unit 26. The slit 271 is placed at a focusing position of the white light or the monochromatic light so that the white light or the monochromatic light is passed through the detection lens 263 and enters into an effective area of the diffraction grating 272. The diffraction grating 272 separates the white light or the monochromatic light passed through the slit 271 in each of prescribed directions for each of the wavelengths of the white light or the monochromatic light.

The light detection unit 28 includes a filter array 281 and a photodiode arrays 282 having a plurality of light receiving elements. The filter array 281 avoids strayed lights. Each of the plurality of light receiving elements in the photodiode array 282 converts a plurality of lights of preliminarily selected wavelengths in the white light or the monochromatic light supplied from the spectroscopic analysis unit 27 to the electric detection signals. The converted detection signals are supplied to the signal processing unit 29. The plurality of preliminarily selected wavelengths comprised of a plurality of wavelengths includes the white light from the white light source 211 (hereinafter, "wavelengths corresponding to the white light") and the first to third wavelengths of the first to third monochromatic lights from the first to third monochromatic light sources 221, 222 and 223, but excluding the wavelengths corresponding to the white light (hereinafter, "wavelengths corresponding to the monochromatic light").

In the case where the lighting direction setting unit 24 is comprised of a half mirror or a light polarizing filter, it is possible to use a monochromatic light source for irradiating a monochromatic light of the same wavelength in the wavelengths corresponding to the white light.

The signal processing unit 29 converts each detection signal supplied from the plurality of light receiving elements of the photodiode array 282 to digital signals in order to generate reference sample data or object sample data. The generated reference sample data or object sample data are supplied to the data processing unit 50.

As explained above, since the light source unit 20 of the automatic analysis apparatus consistent with the present invention includes a white light source unit 21 for measuring changes of color tones at various wavelength bands and a monochromatic light source unit 22 for measuring turbidity changes, it becomes possible to perform measurements by selectively changing the light with respect to a mixed solution of the sample and at least one reagent in the reaction cuvette 3 placed in an analyzing unit 18. Thus, in the case of changes of color tone due to the degree of light absorption at particular wavelengths occur as a result of the particular reaction between the sample and the at least one reagent in the reaction cuvette 3, the mixed solution is measured by using the white light. If turbidity changes occur in the mixed solution in the reaction cuvette 3, the mixed solution is measured by using the monochromatic light.

Although the automatic analysis apparatus consistent with the present invention has two kinds of light sources, it is possible to use the same optical system for white light measurements by using the monochromatic light. Thus, the optical system including a lighting direction setting unit 24, a lighting optical unit 25, a detection optical unit 26, a spectroscopic analysis unit 27 and a detection unit 28 can be used for both measurements by using different light sources. Consequently, a multiuse automatic analysis apparatus can be achieved with a simplified compact structure.

FIGS. 6A and 6B show examples of analysis conditions setting screens displayed on the display unit 62 in order to explain the setting of analysis conditions for items to be measured by selectively using a white light or at least one monochromatic light. FIG. 6A shows an example of analysis conditions for a biochemical item to be measured. In the biochemical analysis conditions setting screen 63, a plurality dialogue boxes 631 to 639 are displayed. Thus, the "ITEM" dialogue box 631 displays a name of an item to be measured, the "SAMPLE AMOUNT" dialogue box 632 and the "REAGENT AMOUNT" dialogue boxes 633 and 634, respectively, indicate amount of sample and reagent for using a reaction. The "KIND OF REACTION" dialogue box 636 shows a measuring type of reaction either for spectrophotometry or turbidimetric immunoassay, the two "WAVELENGTH" dialogue boxes 636 and 637 indicate the detecting wavelengths and "LIGHT MEASURING POINT" dialogue boxes 638 and 639 show measuring points P in the analysis unit 18 (FIG. 2).

By operating the operation unit 70, a plurality of analysis conditions for an item to be measured is inputted in each of the dialogue boxes 631 to 639 on the biochemical analysis conditions setting screen 63. The inputted analysis conditions are stored in a memory circuit of the system control unit 80.

In the example of FIG. 6A, as an item to be measured for a biochemical analysis using a white light, in the "ITEM" dialogue box 631 "GOT" (Glutamate Oxalo-acetate Transaminase) is inputted. To measure the item "GOT", the necessary amount of the object sample is inputted as 5 μl (microliter) and the dialogue box 632 displays "5".

The "REAGENT AMOUNT" column displays a dialogue box 633 for indicating an amount of the first reagent and the dialogue box 633 for indicating an amount of the second reagent 634. If a single reagent type measurement is required, the first reagent dialogue box 633 displays the necessary amount of the first reagent. If the measurements of the two reagents are required, both the first reagent dialogue box 633 and the second reagent dialogue box 634 display the necessary amount of the first and second reagents, respectively. To measure the item "GOT", since the two-reagent-type measurement is employed, an amount of 150 μl is inputted for the first reagent and an amount of 50 μl is inputted for the second reagent. Thus, the first reagent dialogue box 633 displays "150" and the second reagent dialogue box 634 displays "50".

In the "KIND OF REACTION" dialogue box, a reaction mode for measuring the mixed solution of the object sample and the reagent that are set as the item in the "ITEM NAME" dialogue box in order to determine the light source for performing the measurement. For instance, a reaction mode for "GOT" is typically analyzed by detecting a change of color tone at a particular wavelength due to a light absorption degree. Accordingly, "SPECTRO PHOTOMETRY" is displayed in the "KIND OF REACTION" dialogue box 635 by selectively inputting spectrophotometry. Based on this setting of the light source, the light measuring unit 13 performs a measurement using the white light.

As the "WAVELENGTH" item, a "WAVELENGTH 1" dialogue box and a "WAVELENGTH 2" dialogue box are displayed for setting each wavelength in accordance with the item to be measured displayed in the "ITEM NAME" dialogue box. If "SPECTRO PHOTOMETRY" is set in the "KIND OF REACTION" dialogue box, one or two different wavelengths corresponding to the wavelengths of the white light are selected. Since a particular change of a light absorption degree due to a particular reaction between the item to be measured "GOT" item and the reagent item occurs at a particular wavelength, for instance, 340 nm (nanometers), the particular wavelength or the nearest wavelength is inputted. Accordingly, "340" is displayed in the "WAVELENGTH 1" dialogue box 636. In the "WAVELENGTH 2" dialogue box, as a reference wavelength, for instance, a wavelength of 380 nm is inputted since a change of the absorption degree due to the reaction between the "GOT" item and the reagent item does not occur or is slight at that wavelength. Thus, "380" is displayed in the "WAVELENGTH 2" dialogue box 637.

When the brightness of the white light of a particular wavelength set in the "WAVELENGTH 1" dialogue box or the nearest wavelength is weak for a particular reaction of the solution, it is possible to set a particular monochromatic light having the same wavelength to a particular wavelength by selecting among the first to third monochromatic lights in order to perform a measurement in the light measuring unit 13 by using the monochromatic light. This can increase a detection signal level in the detection unit 28 without the use of the white light. Consequently, it becomes possible to perform a spectrophotometric test at the particular wavelength with highly precise measurements.

In the "MEASURING POINT" dialogue box, a light measuring timing of the mixed solution for the item inputted in the "ITEM" dialogue box. For instance, when the twentieth to twenty-ninth light measuring points are inputted as the first and last light measuring timings "20" and "29" are displayed in the dialogue boxes 638 and 639, respectively. The first light measuring point means the first point that the reaction cuvette 3 (FIG. 2), which contained an object sample, is rotated in an R1 direction, as shown in FIG. 3, and first crosses the light measuring position P in the analyzing unit 18. Thus, the light measurements at the twentieth to twenty-ninth light measuring points means that the light measuring unit 13 generates object sample analysis data of ten (10) at every timing when the reaction cuvette 3 contained the measuring object sample passes the light measuring position P twenty to twenty-nine times. Based on the generated 10 object sample data, "GOT" is analyzed.

FIG. 6B shows an example of an immune serum analysis conditions setting screen 64 by using the monochromatic light. Similar to the biochemical analyzing conditions setting screen 63, the immune serum analysis conditions setting screen 64 also displayed a plurality of dialogue boxes 641 to 649 for displaying a plurality of setting data based on a plurality of input operation instructions. As an example of a turbidimetric immunoassay item, it is supposed that a C-Reactive Protein is inputted and "CRP" is displayed in the "ITEM" dialogue box 641. To measure the CRP, for instance, an object sample of amount 3 μl is inputted. Accordingly, "3" is displayed in the "SAMPLE AMOUNT" dialogue box 642.

To measure the CRP, typically, two kinds of reagents are used. In this case, a first reagent of amount 100 μl and a second reagent of amount 50 μl are inputted. Accordingly, "100" and "50" are in the "FIRST REAGENT" dialogue box 643 and the "SECOND REAGENT" dialogue box 644. If the turbidimetric immunoassay due to a latex agglutination reaction is instructed so as to apply for a measurement of the CRP, "TURBIDIMETRY" is displayed in the "KIND OF REACTION" dialogue box 645.

When the turbidimetric immunoassay is inputted in the "KIND OF REACTION" dialogue box, one or two monochromatic lights corresponding to one or two different wavelengths selected among the first to third monochromatic lights are inputted in the "WAVELENGTH" dialogue box.

For instance, when the first monochromatic light is selected in order to measure a C-Reactive Protein, "FIRST MONOCHROMATIC LIGHT" is displayed in the dialogue box 646 of "WAVELENGTH 1". Similarly, if the second monochromatic light also selected to measure the "CRP", "SECOND MONOCHROMATIC LIGHT" is displayed in the dialogue box 647 of "WAVELENGTH 2". By these setting operations, the light measuring unit 13 performs measurements on the "CRP" by using both the first monochromatic light and the second monochromatic light.

For a "MEASURING POINT" item, measuring timings of the mixed solution containing C-Reactive Protein are selected. For instance, when the thirty-third to thirty-fifth light measuring points are inputted, "33" and "35" are displayed in the dialogue boxes 648 and 649, respectively. Thus, a total of three measurements are performed at each of the thirty-third to thirty-fifth light measuring points when the reaction cuvette 3 contained the measuring mixed solution passes each of the light measuring position P. Accordingly, the light measuring unit 13 generates three object sample data for the "CRP" and analysis data is generated based on the object sample data.

Operations of the automatic analysis apparatus 100 consistent with the present invention will be explained next. The data memory unit 52 of the data processing unit 50 (FIG. 1) stores a plurality of calibration curves generated by measuring a plurality of reference samples for each of the items to be measured. When a particular item to be measured is set by inputting operation through the operation unit 70, the item to be measured is displayed on the display unit 62 and also the item to be measured is stored in the memory circuit of the system control unit 80.

Figure 7:
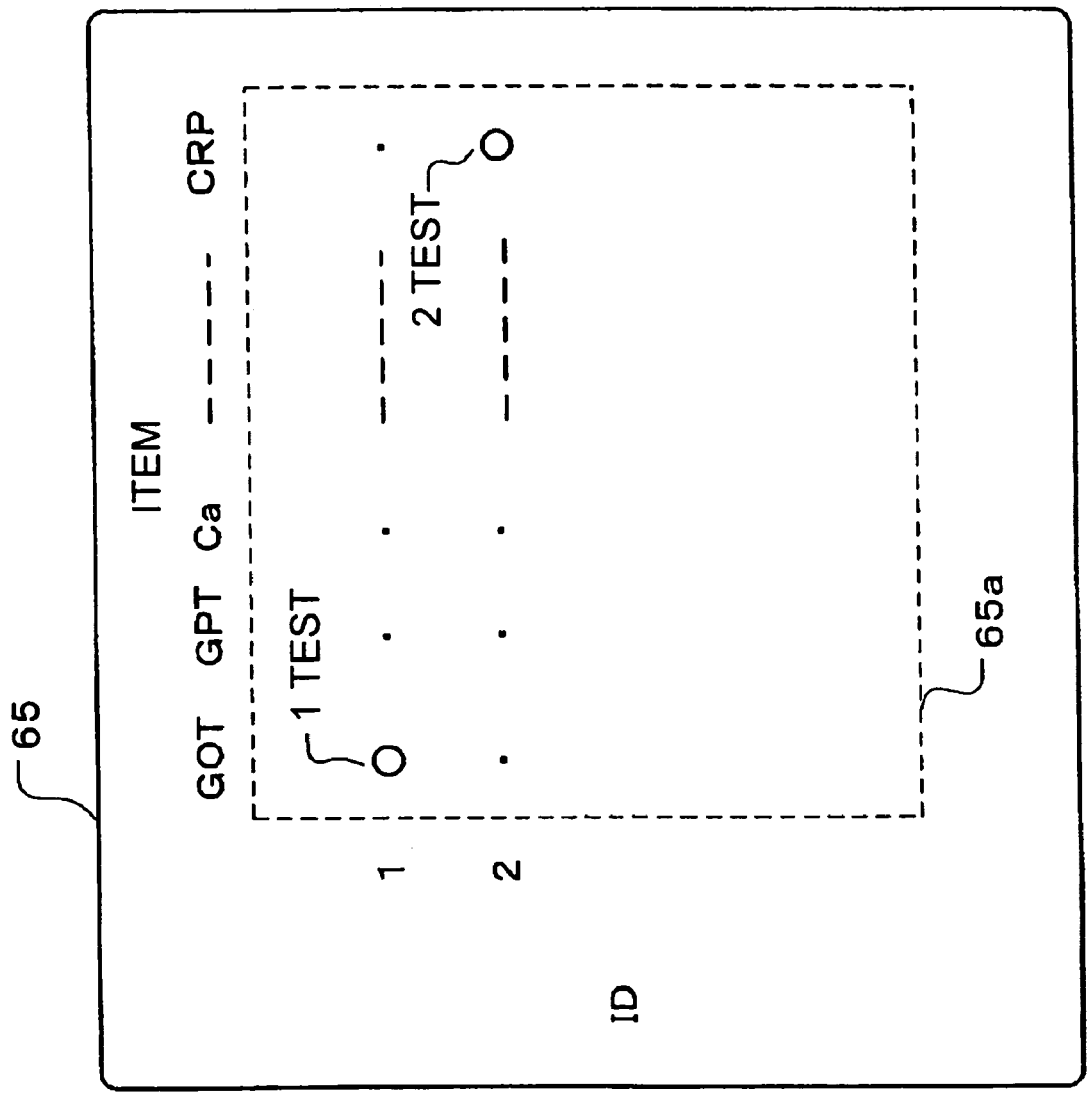
FIG. 7 illustrates an example of a setting screen displaying the inputted analysis conditions for an item to be measured as shown in FIGS. 6A and 6B

FIG. 7 is an example of the item to be measured setting screen displayed on the display unit. The item to be measured setting screen 65 includes an object "ID" column that is set by an object data, an "ITEM" column in order to display items to be measured that are inputted through the biochemical analysis conditions setting screen 63 (FIG. 6A) and the immune serum analysis conditions setting screen 64 (FIG. 6B) and an item to be measured setting area 65a for displaying the selected items in the "ITEM" column for each object as designated in the "ID" column.

In the "ID" column, for instance, Nos. "1" and "2" are preliminarily inputted as the object IDs. In this embodiment, for instance, "GOT", "GPT" (Glutamate Pyruvate Transaminase), "Ca" (calcium) and so on are inputted in the "ITEM" column as the biochemical analysis items. Further, as the turbidimetric immunoassay item, for instance, "CRP" (C-Reactive Protein) is inputted and "CRP" is displayed in the "ITEM" column.

In the item to be measured setting area 65a, a circle mark "○" is displayed at a selected position among the items listed in the "ITEM" column for each of objects listed in the "ID" column and a dot mark "•" is displayed at the nonselected positions corresponding to each of the items and the objects. For instance, a biochemical analysis item "GOT" in the "ITEM" column is selected for an object "1" in the "ID" column by an input operation through the operation unit 70. At the crossing point of the object "1" and the "GOT" in the item to be measured setting area 65a, a circle mark "○" is displayed as "1 TEST". Similarly, when an immune serum analysis item "CRP" listed in the "ITEM" column is selected for an object "2" listed in the "ID" column, a circle mark "○" is displayed as "2 TEST" at the crossing point of the object "2" and the "CRP" in the item to be measured setting area 65a.

The setting item data selected in the item to be measured setting screen 65 are stored in a memory circuit in the system control unit 80. A measurement of an object sample is successively performed from the item "1 TEST" based on the stored setting item data.

Figure 8:
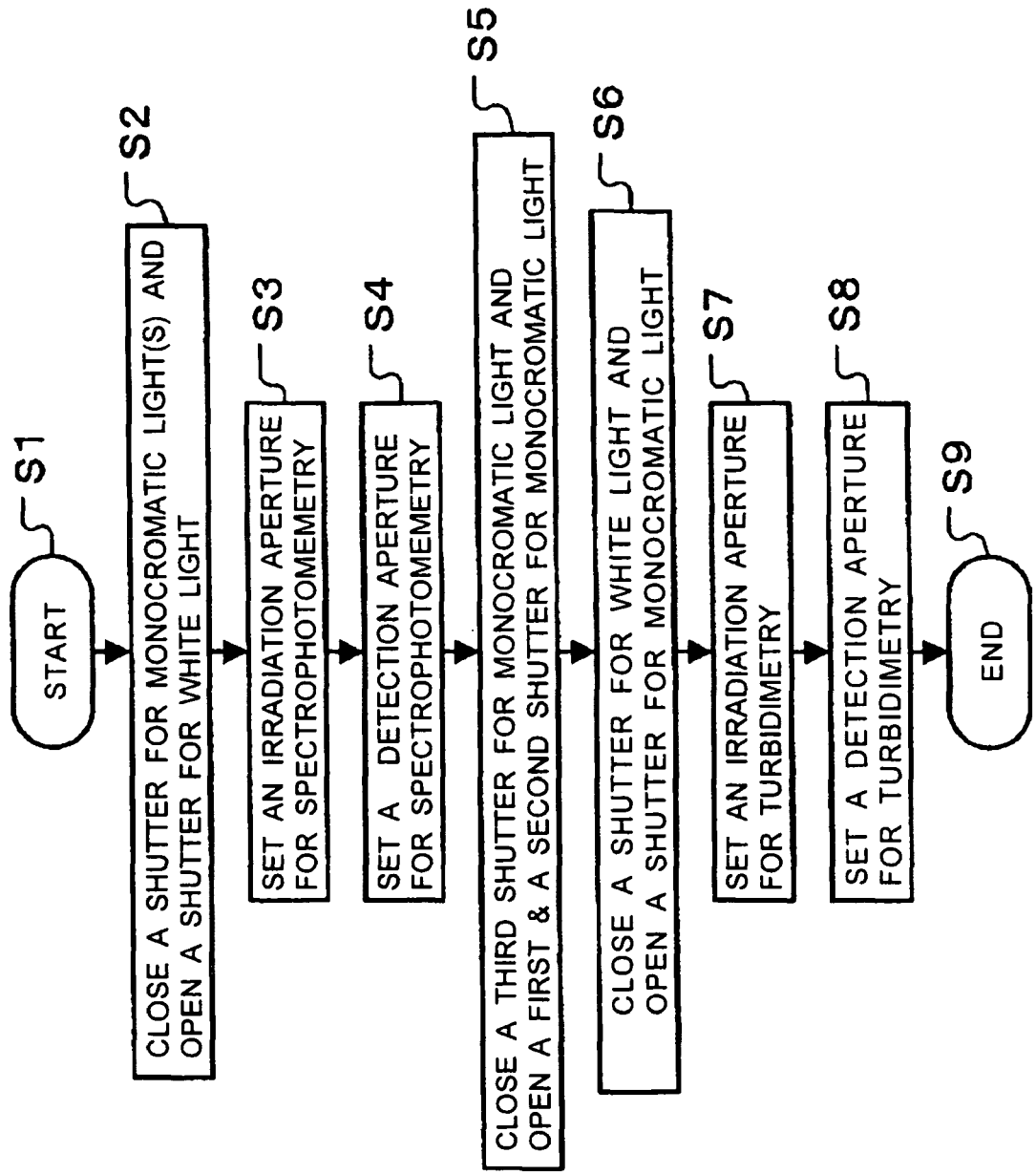
FIG. 8 is a flowchart illustrating an embodiment of a light measuring operation in an automatic analysis method consistent with the present invention.

FIG. 8 is a flowchart for explaining a measuring operations of the automatic analysis apparatus 100. Firstly, as illustrated in FIG. 2, two object sample containers $17_1$, $17_2$ containing of the object IDs "1" and "2" are placed on the disk sampler 5 of the analyzing unit 18. The measuring operation of the object sample is started by instructing through the operation unit 70 (FIG. 8, step S1).

Based on each of analysis conditions that are set by the biochemical analysis conditions setting screen 63 (FIG. 6A) and the immune serum analysis conditions setting screen 64 (FIG. 6B), 63 (FIG. 6A) and also the item to be measured data that are set by the item to be measured setting screen 65 (FIG. 7), the system control unit 80 (FIG. 1) issues measuring instruction signals for each of the object samples to the analysis control unit 40, the data processing unit 50 and the output unit 60. By receiving the command signals from the system control unit 80, the drive control unit 42 in the analysis control unit 40 drives each of the mechanisms in the mechanism unit 41 in order to operate each unit in the analyzing unit 18.

For instance, in FIG. 2, the sample dispensing probe 16 of the analyzing unit 18 dispenses object samples corresponding to "1 TEST" and "2 TEST" set in the item to be measured setting screen 65 (FIG. 7) from the sample containers $17_1$ and $17_2$ to each of the reaction cuvettes $3_1$ and $3_2$. After dispensing the object samples, the first reagent dispensing probe 14 dispenses the first reagent corresponding to the items to be measured for the "1 TEST" and "2 TEST" from the reagent container 6 in the first reagent warehouse 1 to each of the reaction cuvettes $3_1$ and $3_2$. After dispensing the first reagent, the stirring unit 11 stirs the mixed solution of the object sample and the first reagent contained in each of the reaction cuvettes $3_1$ and $3_2$.

After stirring the mixed solution, the second reagent dispensing probe 15 dispenses a second reagent corresponding to the item to be measured for the "1 TEST" and "2 TEST" from the reagent container 7 in the second reagent warehouse 2 to each of reaction cuvettes $3_1$ and $3_2$ dispensed with the first reagent. After dispensing the second reagent, the stirring unit 11 stirs the mixed solution in each of the reaction cuvettes $3_1$ and $3_2$. After stirring the object sample corresponding to the "1 TEST" and "2 TEST" with the first reagent and second reagent, each of the reaction cuvettes $3_1$ and $3_2$ containing the stirred mixed solution is transferred to the light measuring unit 13 in order to measure the mixed solution.

To measure the mixed solution contained in the reaction cuvette $3_1$ corresponding to the "1 TEST", the control unit 42 in the analysis control unit 40 controls the white light shutter 231 and the monochromatic light shutter 23 by driving the mechanism unit 41 in the analysis control unit 40 based on the biochemical analysis conditions of the "KIND OF REACTION" data and the "MEASURING POINT" data (FIG. 6A) for the item to be measured "GOT" that are supplied from the system control unit 80. Thus, in the light exchanging unit 23 of the light measuring unit 13, the monochromatic light shutter 232 is closed and the white light shutter 231 is opened just before the arrival of the reaction cuvette $3_1$ containing the mixed solution corresponding to the "1 TEST" and the light measuring position P 20 to 29 as set by the biochemical analysis conditions setting screen 63 (FIG. 8, step S2). Consequently, the white light from the white light source unit 21 is irradiated to the lighting optical unit 25 through the lighting direction setting unit 24 (FIG. 2).

Figure 9:
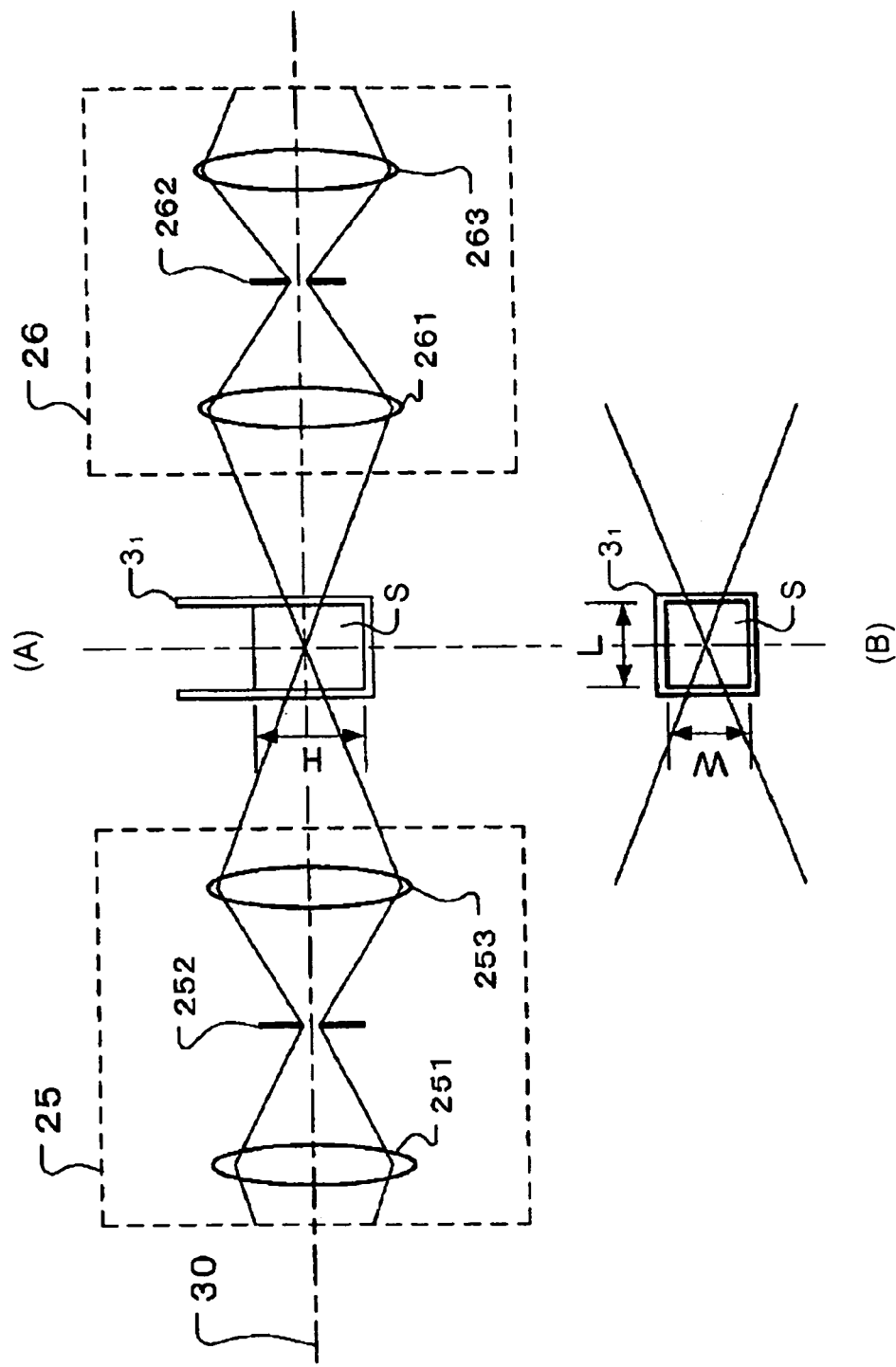
FIG. 9 shows a lighting control of the white light and a control of the detection aperture diaphragm shown in FIG. 3.

FIG. 9 shows how to transmit the white light to the detection optical unit 26 passing through the reaction cuvette $3_1$ containing the mixed solution. The open and close operations for the lighting aperture diaphragm 252 in the lighting optical unit 25 and the detection aperture diaphragm 262 in the detection optical unit 26 are controlled by the analysis control unit 42 based on the data of the sample amount, the reagent amount and the kind of reaction that are set by the biochemical analysis conditions setting screen 63.

The analysis control unit 42 obtains a total amount of 250 µl of the mixed solution for the item to be measured "GOT" by adding the sample amount of 5 µl and the first and second reagent amounts of 150 µl and 50 µl. The inner configuration of the reaction cuvette $3_1$ is a square having a height, a cross sectional view (A) and an upper view (B) is shown in FIG. 9. Suppose that the reaction cuvette $3_1$ has a length of 5 mm (L=5) and a width of 4 mm (W=4), a height H of the mixed solution S is obtained as H=10.25 by dividing the total amount 205 µl with the bottom area (=5 mm×4 mm) of the reaction cuvette $3_1$. Based on the height H, length L and width W of the reaction cuvette $3_1$, the lighting aperture diaphragm 252 of the lighting optical unit 25 is controlled by a lighting aperture for spectrophotometry so that the white light passed through the reaction cuvette $3_1$ can irradiate the mixed solution in a wide range. Further, the detection aperture diaphragm 262 is controlled so as to form a detection aperture for the spectrophotometric test in order to pass the white light of the same scope of irradiation scope on the reaction cuvette $3_1$ determined by the lighting aperture diaphragm 252 through the light detection unit.

By controlling these diaphragms in accordance with the amounts of the sample and the reagent that are set by the analysis conditions setting screen, the irradiation scope of the white light on the reaction cuvette $3_1$ is determined. Thus, when the amount of the mixed solution is small, it is possible to reduce the irradiation scope of the white light on the reaction cuvette $3_1$. Since it possible to reduce the necessary amount of the mixed solution, the necessary amounts of the sample and the reagents can also be reduced. However, as in a case for the biochemical item "GOT", when a relatively large amount of the mixed solution is required in order to increase an accuracy of the measurement in the light measuring unit 13, it is possible to enlarge the irradiation scope of the white light onto the reaction cuvette $3_1$ to increase a detection degree in the light detection unit 28 by increasing the transmitted light.

To prevent the white light from irradiating from the bottom of the reaction cuvette 3 under the mixed solution or a vacant upper portion of the reaction cuvette 3, a minimum necessary amount of the mixed solution is determined for the respective measurements.

As explained above, the lighting aperture diaphragm 252 in the lighting optical unit 25 is set so as to form a lighting aperture size for irradiating the white light for the spectrophotometric item "GOT" (FIG. 8, step S3). The white light irradiated through the lighting direction setting unit 24 are condensed on the lighting aperture diaphragm 252 through the first lighting condensing lens 251. After passing though the lighting aperture diaphragm 252 of a controlled lighting aperture size for spectrophotometry, the white light is condensed onto the mixed solution in the reaction cuvette 3 at light measuring position P through the second lighting condensing lens 253.

In the detection optical unit 26, an aperture of the detection aperture diaphragm 262 is set to a detection aperture size for the spectrophotometric test of "GOT" (FIG. 8, step S4). The transmitted light through the reaction cuvette 3 is condensed on the detection aperture diaphragm 262 by the first detection light condensing lens 261. By passing through the sized aperture of the detection aperture diaphragm 262, the white light is irradiated onto the spectroscopic analysis unit 27 through the second detection light condensing lens 263.

In the spectroscopic analysis unit 27, the light transmitted through the reaction cuvette 3 and the slit 271 is separated into each wavelength by a diffraction grating 272. A plurality of photodiode arrays 282 in the light detection unit 28 detects each of the separated lights of wavelengths 340 nm and 380 nm that correspond to the separated spectrophotometric detection wavelengths for testing "GOT" by the diffraction grating 272. Based on the detection signals, a signal processing unit 29 in the light measuring unit 13 generates object sample data. The object sample data generated from the light measuring unit 13 are supplied to the data processing unit 50.

A calculation unit 51 in the data processing unit 50 obtains a difference between the object sample data generated from the light measuring unit 13 by subtracting the object sample data of wavelength 340 nm from the object sample data of wavelength 380 nm. Then, the calculation unit 51 reads out a preliminary stored calibration curve of the "GOT" from the memory unit 52. By using both of the read out "GOT" calibration curve and the difference of the object sample data, "GOT" analysis data is generated. The generated analysis data is stored in the memory unit 52 of the data processing unit 50 and also is outputted to the output unit 60.

When the mixed solution dispensed into the reaction cuvette 3 is the item "CRP", a measurement for the No. 2 of the turbidimetric immunoassay analysis conditions is performed. To control the each of shutters in the monochromatic light source unit 22 and the light exchanging shutter in the light exchanging unit 23, the drive control unit 42 in the analysis control unit 40 drives the mechanism unit 41 based on each of the "CRP" analysis condition data relating to the "KIND OF REACTION" and the "MEASURING POINT" supplied from the system control unit 80.

At the third to fifth light measuring points that are set by the immune serum analysis conditions setting screen 64, the monochromatic light source unit 22 closes the third monochromatic light shutter 227 and opens the first and second monochromatic light shutters 225 and 22 just before the arrival of the reaction cuvette $3_2$ containing the No. 2 test "CRP" mixed solution to the light measuring position P (FIG. 8, step S5). Thus, the first and second monochromatic lights irradiated from the first and second monochromatic light sources 221 and 222 are multiplexed by first multiplexing unit 228 and irradiated onto the light exchanging unit 23. The light exchanging unit 23 closes the white light shutter 231 and opens the monochromatic light shutter 232 (FIG. 8, step S6).

Consequently, the multiplexed first and second monochromatic lights in the monochromatic light source unit 22 are reflected through the lighting direction setting unit 24 so as to irradiate to the lighting optical unit 25 along the first light axis 30. Based on the "KIND OF REACTION" data for a "CRP" supplied from the system control unit 80, the control unit 42 in the analysis control unit 40 controls the aperture sizes of the lighting aperture diaphragm 252 in the lighting optical unit 25 and the detection aperture diaphragm 262 in the detection optical unit 26.

Figure 10:
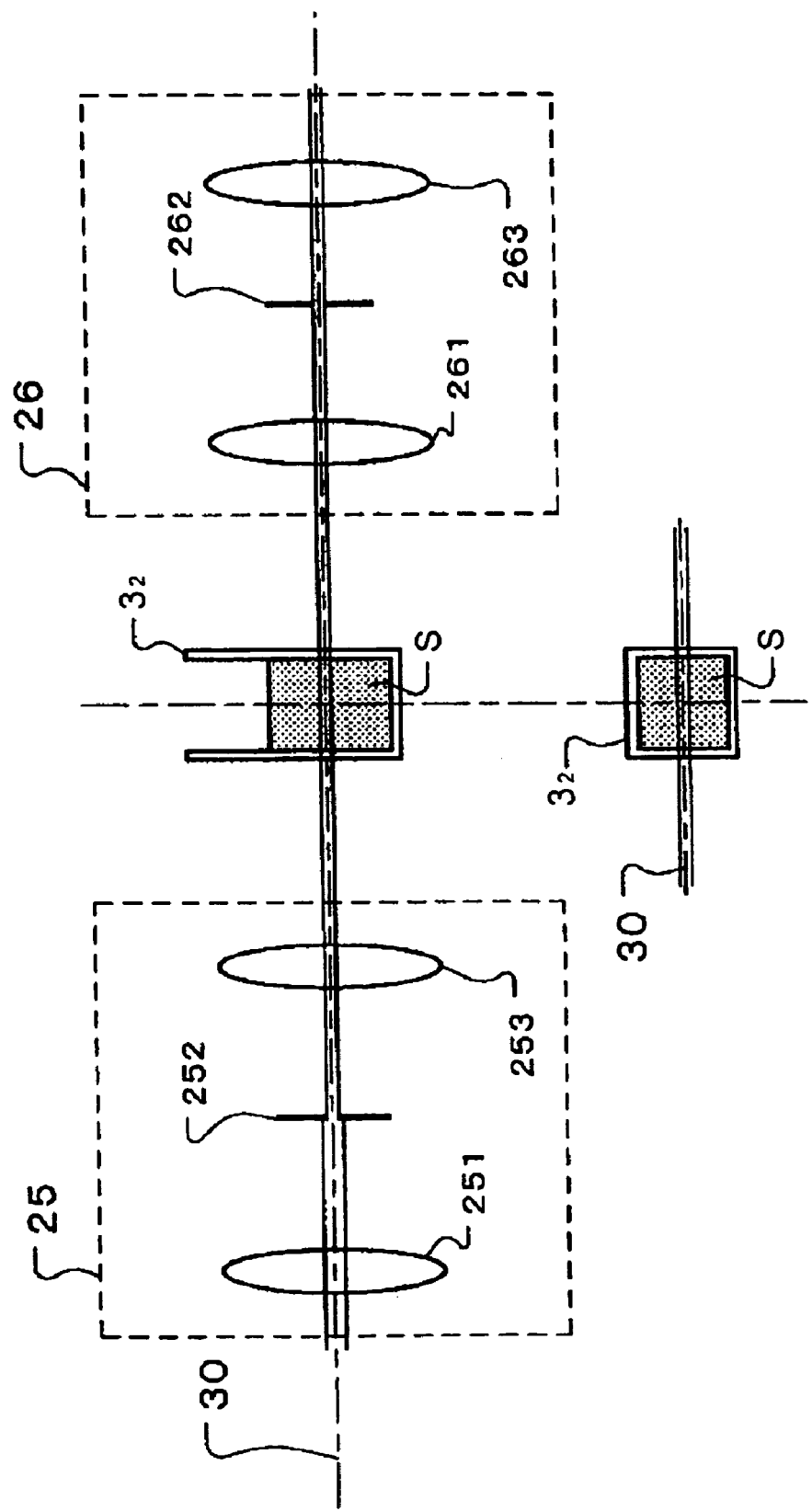
FIG. 10 shows a lighting control of the monochromatic light and a control of the detection aperture diaphragm shown in FIG. 3.

FIG. 10 illustrates a measurement of a monochromatic light by controlling each aperture size of the lighting aperture diaphragm 252 and the detection aperture diaphragm 262. As depicted in FIG. 10, the lighting aperture of the lighting aperture diaphragm 252 is set so that an incident of the multiplexed monochromatic lights passing through the analysis first irradiating light condensing lens 251 by a drive control of the control unit 40 forms a fine beam for the turbidimetry measurement passing straight along the first light axis 30 (FIG. 8, step S7). The multiplexed first and second monochromatic lights passed through the lighting aperture diaphragm 252 are irradiated into the mixed solution contained in the reaction cuvette $3_2$ through the second irradiate light condensing lens 253 on the first light axis 30 for measuring a turbidity of the mixed solution due to, for instance, latex agglutinations.

The detection aperture diaphragm 262 in the detection optical unit 26 sets a detection aperture for performing a turbidimetry test so as that the monochromatic light passed through the reaction cuvette $3_2$ has the same irradiation scope as the lighting scope determined by the lighting aperture diaphragm 252 on the reaction cuvette $3_2$ (FIG. 8, step S8). The detection aperture diaphragm 262 allows the incident light to pass that is only transmitted along a parallel to the first light axis 30 among the monochromatic light including scattered lights transmitted through the first detection light condensing lens 261 and the incident light passed through the second detection light condensing lens 263 is irradiated to the spectroscopic analysis unit 27.

By setting the lighting aperture diaphragm 252 and the detection aperture diaphragm 226 for the turbidity test, the monochromatic light is irradiated onto the mixed solution in the reaction cuvette $3_2$ in order to transmit the penetrated light to the spectroscopic analysis unit 27. The incident light transmitted through the slit 271 of the spectroscopic analysis unit 27 is separated into each of wavelengths through the diffraction grating 272. The detection unit 28 detects each light corresponding to each of the wavelengths of the first monochromatic light and the second monochromatic light separated through the spectroscopic analysis unit 27. The detection signals are outputted to the signal processing unit 29. The signal processing unit 29 generates each of the object sample data based on the detection signals. The object sample data is outputted to the calculation unit 51.

The calculation unit 51 in the data processing unit 50 reads a calibration curve for "CRP" that is preliminarily prepared and stored in the memory unit 52. Further, the calculation unit 51 generates analysis data based on the read calibration curve and each object sample data corresponding to each of the first and second monochromatic lights outputted from the signal processing unit 29. The generated analysis data is stored in the memory unit 52 of the data processing unit 50 and is outputted to the output unit 60. Such measurements of turbidity of the mixed solution the use a plurality of monochromatic lights can generate analysis data with higher reliability.

If it is previously known that a large difference of absorption exists between two object sample data, it is possible to generate analysis data of an object sample data with high reliability by using a calibration curve that is preliminarily prepared based on the difference of one data of the object sample and the data of two monochromatic lights.

After a measurement, the washing unit 12 (FIG. 3) in the analyzing unit 18 is activated and the mixed solution is suctioned from the reaction cuvette. The reaction cuvette is then washed and dried. The automatic analysis apparatus 100 finishes the measurement at a time when the output unit 50 outputs analysis data of each item for the object IDs "1" and "2", and the washing and drying of the all reaction cuvettes 3 (FIG. 8, step S9).

As explained above, the automatic analysis apparatus consistent with the present invention provides a light source in that both a white light source unit and a monochromatic light source unit are provided at an early stage of a lighting optical system in the light measuring unit. The automatic analysis apparatus consistent with the present invention can perform both measurements under different of analysis conditions, for example, a change of color tone and a change of turbidity, by selectively exchanging the white light or the monochromatic light on the same light axis, or by irradiating both the white light and the monochromatic light. It is possible to select wavelengths of the monochromatic light source by providing a plurality of monochromatic light sources of a plurality of wavelengths so as to form a multiplexing optical system for each of the plurality of monochromatic light rays on the same light axis.

According to the automatic analysis apparatus consistent with the present invention, it becomes possible to commonly use the lighting unit, the light detection unit, the spectroscopic analysis unit and the detection unit for measuring spectrophotometry for biochemical tests to the turbidimetric immunoassay measurement by using at least one monochromatic light. Consequently, a simplified automatic analysis apparatus can be constructed for performing measurements under different analysis conditions.

According to the automatic analysis equipment consistent with the present invention, the slit mechanism is provided for exchanging aperture sizes of the lighting aperture and the detection aperture in accordance with the measurement by using the white light of the monochromatic light. Thus, it becomes possible to variably set the measuring conditions in each of the item to be measured by selecting the light source, measuring wavelengths and aperture sizes of the lighting aperture and the detection aperture.

According to the automatic analysis apparatus consistent with the present invention, it can appropriately determine a light passing aperture of the lighting aperture diaphragm and the detection aperture diaphragm based on the inputted necessary amounts for each of the sample and at least one reagent in accordance with the lighting source data. Accordingly, it can measure the change of the solution in the reaction cuvette, with high precision, the minimum amounts of the sample and the reagent.

According to the automatic analysis apparatus consistent with the present invention, the monochromatic light source includes a plurality of monochromatic light sources of different wavelengths so as to form a multiplexing optical system along the same light axis in order to selectively change a different wavelength for the monochromatic light source and also to use a plurality of different wavelengths at the same time. Since it becomes possible to perform the turbidity measurement of a mixed solution in a reaction cuvette by using a plurality of monochromatic lights, it can generate analysis data with high precision.

It is also possible to install light receiving elements in the detection unit of the automatic analysis apparatus consistent with the present invention for exclusively using for a turbidimetric immunoassay measurement.

Other embodiments consistent with the present invention will be apparent to those skilled in the art from consideration of the specification and practice of the present invention disclosed herein. It is intended that the specification and examples be considered as exemplary only, with a true scope and spirit of the present invention being indicated by the following claims.

What is claimed is:

1. An automatic analysis equipment including a light measuring unit configured to measure ingredients in a mixed solution of an object sample and at least one reagent contained in a reaction cuvette by emitting a light and detecting the light transmitted through the reaction cuvette, the light measuring unit comprising:
   a light source unit including a white light source unit configured to emit a white light and a monochromatic light source unit configured to emit at least one monochromatic light;
   a lighting direction setting unit configured to irradiate a light on the reaction cuvette positioned at a measuring point in the light measuring unit by selectively exchanging the white light or the at least one monochromatic light on a measuring light axis in the light measuring unit in accordance with a measuring item;
   a spectroscopic analysis unit configured to perform a spectroscopic analysis of a prescribed wavelength light in the white light or the at least one monochromatic light that are transmitted through the reaction cuvette; and
   a light detection unit configured to detect the prescribed wavelength in the white light or the at least one monochromatic light that are performed spectroscopic analysis in the spectroscopic analysis.

2. The automatic analysis equipment according to claim 1, wherein;
   the monochromatic light source is comprised:
   a plurality of monochromatic light sources, each of monochromatic light sources emits a monochromatic light having a respectively different wavelength; and
   a multiplexing optical system for emitting the white light and at least one monochromatic light selected among the plurality of monochromatic light sources along an analysis light axis of the equipment, wherein
   the detection unit includes a plurality of light receiving elements for detecting lights of prescribed wavelengths of the white light and at least one of the plurality of monochromatic lights.

3. The automatic analysis equipment according to claim 1, wherein;
   the light measuring unit includes:
   a light exchanging unit configured to selectively exchange the white light or the at least one monochromatic light; and
   an irradiating direction setting unit configured to emit the exchanged white light or the at least one monochromatic light so as to irradiate along the same light axis.

4. The automatic analysis equipment according to claim 1, wherein;
   the light measuring unit includes an irradiation optical unit provided between the irradiating direction setting unit and the reaction cuvette; the irradiation optical unit includes a lighting aperture diaphragm configured to set an irradiation scope onto the reaction cuvette;
   the light detection unit includes a detection aperture diaphragm configured to set a passing scope of the white light or the selected at least one monochromatic light transmitted through the reaction cuvette.

5. The automatic analysis equipment according to claim 3, further including:
   an analysis conditions setting unit configured to set lighting data for irradiating the white light or the selected at least one monochromatic light onto the reaction cuvette and each amounts of the object sample and the at least one reagent for dispensing into the reaction cuvette;
   a control unit configured to control operation signals of the equipment based on analysis conditions inputted through the analysis conditions setting unit; and
   wherein:
   the light exchanging unit exchanges the light source to the white light based on a command signal from the control unit in accordance with the lighting data through the analysis conditions setting unit; and
   the lighting aperture diaphragm determines a lighting path so as to pass the irradiated white light through the mixed solution contained in the reaction cuvette based on a control signal of the control unit in accordance with the amount data of the object sample and the at least one reagent determined by the analysis conditions setting unit and preliminary inputted size data of the reaction cuvette.

6. The automatic analysis equipment according to claim 5, wherein;
   the light exchanging unit exchanges the light source to the at least one monochromatic light based on lighting data instructed by the analysis conditions setting unit; and
   a detection aperture diaphragm sets an irradiation area of the monochromatic light passed though the reaction cuvette so as to pass the monochromatic light of a same or similar scope of an irradiation scope determined by a lighting aperture unit.

7. The automatic analysis equipment according to claim 5, wherein;
   the control unit controls so that the lighting aperture determined by the lighting aperture diaphragm and the detection aperture determined by the detection aperture diaphragm have the same opening.

8. The automatic analysis equipment according to claim 1, wherein;
   the detection unit is comprised of a plurality of light receiving elements configured to detect the white light of preliminary determined wavelength lights and the at least one monochromatic light that are divided by the spectroscopic analysis unit.

9. The automatic analysis equipment according to claim 8, wherein;
   the detection unit further includes light receiving elements for using a detection of the turbidity.

10. An automatic analysis method for measuring a mixed solution of an object sample and at least one reagent contained in a reaction cuvette by irradiating a white light and at least one monochromatic light, each emitted from a white light source or a least one monochromatic light source in order to detect a change of color tone or a turbidity of a transmitted light passed through the mixed solution, including:
    irradiating the white light and the at least one monochromatic light onto the reaction cuvette positioned at predetermined light measuring positions by selectively exchanging the white light or the at least one monochromatic light along a same measuring light axis; and detecting the white light of particular determined wavelengths or the at least one monochromatic light transmitted through the reaction cuvette along the measuring light axis detecting the white light of particular determined wavelengths or the at least one monochromatic light transmitted through the reaction cuvette along the measuring light axis.

11. The automatic analysis method according to claim 10, further including;

setting an irradiating direction of the selectively exchanged white light or the at least one monochromatic light so as to irradiate on a same light axis or a same time.

12. The automatic analysis method according to claim 10, further including;

setting an irradiating scope of the white light or the at least one monochromatic light onto the reaction cuvette by a lighting aperture diaphragm; and setting a passing scope of the white light or the at least one monochromatic light through the reaction cuvette by a detection aperture diaphragm.

13. The automatic analysis method according to claim 10, further including;

setting each amounts of the object sample and the at least one reagent for dispensing into the reaction cuvette by an analysis conditions setting unit;

setting a light data for irradiating on the reaction cuvette;

setting analysis conditions for performing measuring items;

exchanging the light source to the white light based on the light data determined by setting the analysis conditions; and setting a light path of the white light irradiate the reaction cuvette so as to transmit the irradiation light passes through the mixed solution contained in the reaction cuvette based on the amount data of the object sample and the at least one reagent determined by setting the analysis conditions.

14. The automatic analysis method according to claim 13, wherein:

exchanging the light source to the at least one monochromatic light based on the light data determined by setting the analysis conditions; and setting a passing scope of the at least one monochromatic light passed through the reaction cuvette by a detection aperture diaphragm based on a control signal so as to transmit a same or similar scope as an irradiation scope determined by setting a lighting aperture.

15. The automatic analysis method according to claim 14, further:

controlling the lighting aperture determined by a lighting aperture diaphragm and a detection aperture determined by the detection aperture diaphragm to be opened under the same opening conditions.

* * * * *